United States Patent
Strauss et al.

(10) Patent No.: US 12,400,738 B2
(45) Date of Patent: *Aug. 26, 2025

(54) WHOLE POOL AMPLIFICATION AND IN-SEQUENCER RANDOM-ACCESS OF DATA ENCODED BY POLYNUCLEOTIDES

(71) Applicant: MICROSOFT TECHNOLOGY LICENSING, LLC, Redmond, WA (US)

(72) Inventors: Karin Strauss, Seattle, WA (US); Yuan-Jyue Chen, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 332 days.

This patent is subject to a terminal disclaimer.

(21) Appl. No.: 18/297,576

(22) Filed: Apr. 7, 2023

(65) Prior Publication Data
US 2023/0245720 A1     Aug. 3, 2023

Related U.S. Application Data

(63) Continuation of application No. 16/024,040, filed on Jun. 29, 2018, now Pat. No. 11,651,836.

(51) Int. Cl.
*G16B 30/00* (2019.01)
*G16B 50/00* (2019.01)

(52) U.S. Cl.
CPC ............ *G16B 30/00* (2019.02); *G16B 50/00* (2019.02)

(58) Field of Classification Search
CPC ................................ G16B 30/00; G16B 50/00
See application file for complete search history.

(56) References Cited

FOREIGN PATENT DOCUMENTS

WO      WO-2017189914 A1 * 11/2017     ............ B82Y 10/00

OTHER PUBLICATIONS

Goldman, N., Bertone, P., Chen, S., Dessimoz, C., LeProust, E.M., Sipos, B. and Birney, E. Towards practical, high-capacity, low-maintenance information storage in synthesized DNA. nature, 494(7435), pp. 77-80. (Year: 2013).*
Tsaftaris, S.A. and Katsaggelos, A.K.. August. On designing DNA databases for the storage and retrieval of digital signals. In International Conference on Natural Computation (pp. 1192-1201). Berlin, Heidelberg: Springer Berlin Heidelberg. (Year: 2005).*
Bornholt, J., Lopez, R., Carmean, D.M., Ceze, L., Seelig, G. and Strauss, K. March. A DNA-based archival storage system. In Proceedings of the twenty-first international conference on architectural support for programming languages and operating systems (pp. 637-649). (Year: 2016).*
Shin, G., Grimes, S.M., Lee, H., Lau, B.T., Xia, L.C. and Ji, H.P. CRISPR-Cas9-targeted fragmentation and selective sequencing enable massively parallel microsatellite analysis, Nature Communications. 8(1). pp. 1-13, (Year: 2017).*
Communication 94(3) Received for European Application No. 19742101.9, mailed on Feb. 2, 2024, 6 pages.

* cited by examiner

*Primary Examiner* — Olivia M. Wise
*Assistant Examiner* — Janna Nicole Schultzhaus
(74) *Attorney, Agent, or Firm* — Benjamin Keim; Newport IP, LLC

(57) ABSTRACT

This disclosure describes an efficient method to copy all polynucleotides encoding digital data of digital files in a polynucleotide storage container while maintaining random access capabilities over a collection of files or data items in the container. The disclosure further describes a process whereby random-access and sequencing of the polynucleotides are combined in a single step.

19 Claims, 4 Drawing Sheets

WHOLE POOL AMPLIFICATION AND IN-SEQUENCER RANDOM-ACCESS OF DATA ENCODED BY POLYNUCLEOTIDES

CROSS-REFERENCE TO RELATED APPLICATION

This application is a continuation of U.S. patent application Ser. No. 16/024,040, filed Jun. 29, 2018, the content of which application is hereby expressly incorporated herein by reference in its entirety.

BACKGROUND

Current storage technologies can no longer keep pace with exponentially growing amounts of data. Synthetic polynucleotides, such as DNA or RNA, offers an attractive alternative due to its potential information density of up to $\sim 10^{18}$ B/mm$^3$, $10^7$ times denser than magnetic tape, and potential durability of thousands of years. Recent advances in DNA data storage have highlighted technical challenges, in particular, with coding and random access, but have stored only modest amounts of data in synthetic DNA.

SUMMARY

Synthesized polynucleotides can include regions that encode digital data. The digital data can be included in a data file that corresponds to content that can be processed by a computing device, such as audio content, video content, text content, image content, or combinations thereof. The region of a polynucleotide that encodes digital data can be referred to herein as a "payload." As used herein, the "length" of a polynucleotide can refer to the number of nucleotides included in a linear chain of nucleotides that comprises the polynucleotide. Based on the limitations to the lengths of polynucleotides that encode digital data, the digital data may be segmented before the polynucleotides are synthesized. In this way, the lengths of the payloads of the polynucleotides are limited.

In situations where polynucleotides encode segments of digital data of a data file, the individual segments that encode the digital data can each be associated with the data file according to a particular framework. In some implementations, each data file may be associated with a file identifier and the polynucleotides encoding the digital data of the data files include regions that encode the respective file identifiers.

Each data file can be associated with one or more polynucleotide groups. In various implementations, each group of polynucleotides can be associated with an individual, unique group identifier and the individual group identifiers can be associated with the particular data file having digital data that is encoded by the polynucleotides included in the respective groups.

In response to a request to retrieve digital data of one or more data files, the group identifiers corresponding to the one or more data files can be determined. The group identifiers can correspond to primer target regions of the polynucleotides that encode the digital data being requested. Thus, primers that are complementary to the group identifiers can be identified and used in the amplification processes that are part of the retrieval of digital data encoded by polynucleotides. In this way, the polynucleotides that encode the digital data being requested can be selectively amplified and subsequently sequenced and decoded to provide the requested digital data.

However, certain sequencing methods can be destructive, and thus, several of copies of the polynucleotides are needed, as well as an efficient method to copy all polynucleotides in the polynucleotide storage container. In some embodiments, the polynucleotides have universal sequences that correspond to primers that can be used to amplify and replicate or copy the whole pool of polynucleotides in a storage container. The configuration of universal sequences and group identifier regions results in nested primer sequences on all polynucleotides, in which the group identifier regions are nested within the universal sequences. Therefore, provided is a system with two sets of sequences, one set for random access to specifically identify/locate particular data (group identifier) and one common set to access all sequences in a pool for amplification/copying all sequences in the pool.

Random-access via PCR or other methods selects only those files that need to be sequenced. Typically the random-access process is done separately from sequencing procedures, which leads to unnecessary latency and complexity. Provided herein is a method whereby amplification of polynucleotides and sequencing are combined in a single method to yield the requested digital data (random access). Thus, nucleotide sequencing is used to facilitate random access of the selected sequences.

DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
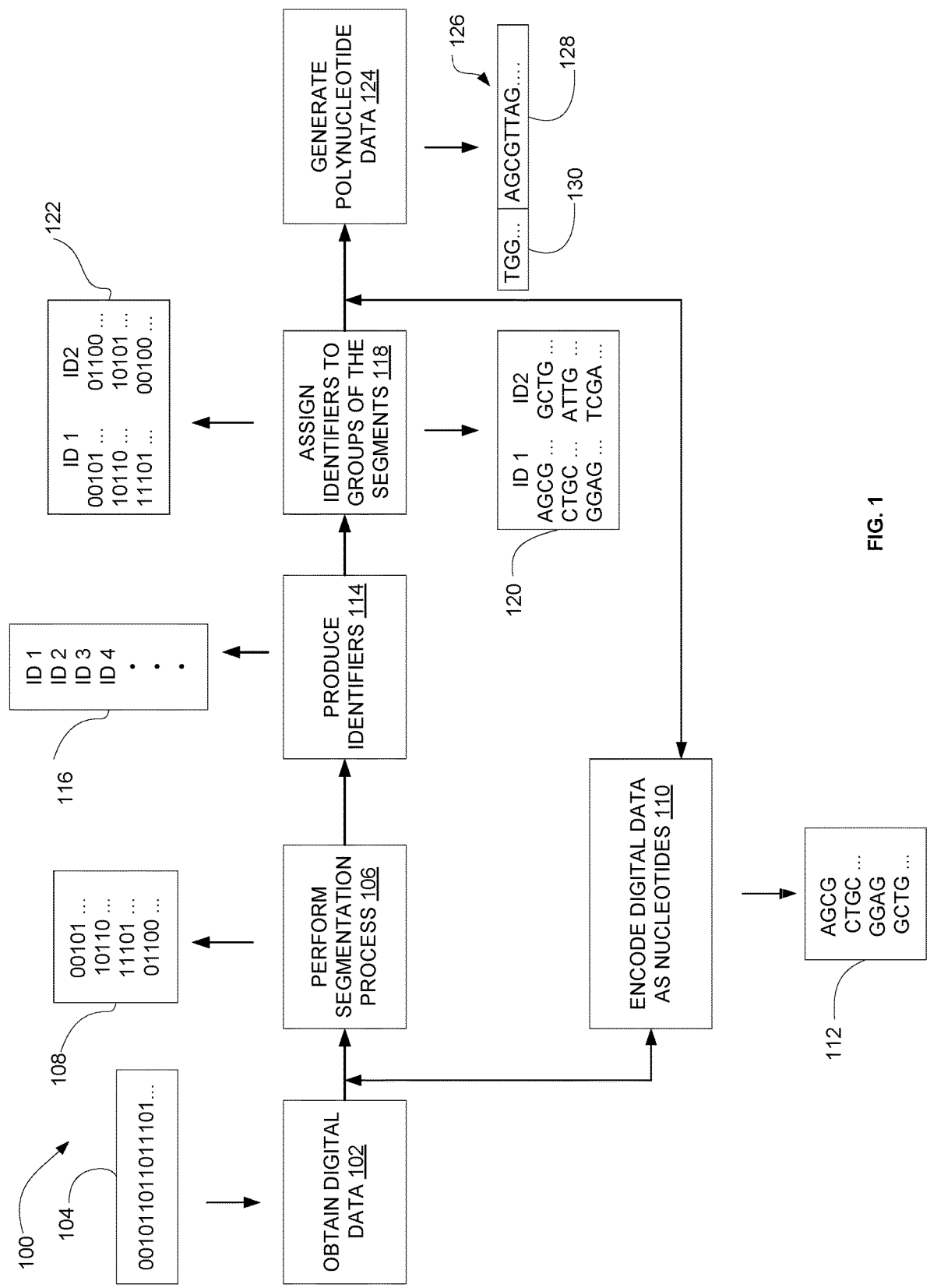
FIG. 1 is a schematic diagram of a process to produce a framework for designing and storing polynucleotides that encode digital data as part of a polynucleotide data storage system.

Much of the data being produced by computing devices is stored on conventional data storage systems that include various kinds of magnetic storage media, optical storage media, and/or solid state storage media. The capacity of conventional data storage systems is not keeping pace with the rates of data being produced by computing devices. Polynucleotides, such as deoxyribonucleic acid (DNA) or ribonucleic acid (RNA), can be used to store very large amounts of data on a scale that exceeds the capacity of conventional storage systems. An arrangement of nucleotides included in a polynucleotide (e.g., CTGAAGT . . . ) can correspond to an arrangement of bits that encodes digital data (e.g., 11010001 . . . ). The digital data can include audio data, video data, image data, text data, software, combinations thereof, and the like.

The retrieval of digital data stored by polynucleotide sequences can be achieved using processes that amplify polynucleotides that encode the digital data that is being requested. For example, polymerase chain reaction (PCR) can be used to amplify polynucleotides that encode the digital data being requested. Amplification of polynucleotides can produce an amplification product that includes an amount of the target polynucleotides being amplified that is several orders of magnitude greater than the original quantity of the target polynucleotides.

The amplification of polynucleotides that encode digital data may be performed selectively such that the polynucleotides encoding the desired digital data are amplified much more than other polynucleotides. To illustrate, polynucleotides of two different data files can be stored in a container of a polynucleotide data storage system and one of the data files can be the subject of a request for digital data. After selective amplification, the number of polynucleotides associated with the requested data file will be orders of magnitude greater than the number of polynucleotides of the other data file. A sample of the amplification product can be sequenced by a sequencing machine and the sequencing data that includes reads from the sequencing machine can be analyzed/decoded to reproduce the original bits of the requested digital data. Although the polynucleotides associated with the data file that was not requested are still present, the probability of sequencing these polynucleotides is very small because there are so many more copies of the polynucleotides from the requested data file. Thus, the polynucleotide sequences included in the sequencing data that correspond to the requested digital data can be identified because they are found in greater quantities than the polynucleotide sequences that are not associated with the digital data request.

This disclosure describes frameworks and techniques to improve random access to digital data encoded by polynucleotides. In particular by combining retrieval and sequencing in a single method to yield the requested digital data (random access). As a result, the inefficiencies in the retrieval of digital data encoded by polynucleotides can be minimized. Also, described herein is the use of universal primers to generate copies all polynucleotides in a storage container at the same time with a single primer pair. Such copies are needed, for example, when retrieval procedures result in the destruction of the polynucleotides.

In situations where digital storage media utilize random access of digital data, digital data stored anywhere on the digital storage media can be accessed without first accessing another portion of the digital data. In contrast, sequential access of digital data comprises the access of digital data in an ordered sequence. Thus, for sequential access of digital data, one or more additional portions of the digital data may be accessed before accessing the requested digital data, while random access of digital data enables the access of the requested digital data without first accessing other portions of the digital data. Random access of digital data can be accomplished by providing address information, such as metadata, for each element of digital data that indicates a storage location for the respective elements of digital data. Upon receiving a request to obtain a portion of the digital data, the addressing information can be accessed and the storage location utilized to obtain the requested digital data from one or more digital storage media.

Random access in the context of polynucleotide data storage systems can take place through encoding addressing information in sequences of polynucleotides. The addressing information can uniquely identify the data encoded by the sequences of polynucleotides. At least a portion of the addressing information can comprise a primer target sequence. In response to a request for particular digital data encoded by polynucleotides, primers that correspond to the primer target sequences of the target polynucleotides can be obtained. The primers can then be utilized to selectively amplify and/or sequence the target polynucleotides in a sample that includes both the target polynucleotides and other polynucleotides that encode digital data other than the requested digital data. The sequences of the target polynucleotides can be decoded to reproduce the requested digital data. As used herein, "primer" refers to a single primer and/or a pair of primers (such as a forward and reverse primer set), unless specifically indicated otherwise. Further, "primer" refers to a nucleotide sequence that is specifically chosen to perform a selection function where the selection function is based on the property that the nucleotide sequence will physically hybridize (attach) to its reverse complement. In some cases, a region of a polynucleotide sequence to which a primer can bind during, for example, a polynucleotide replication technique, can be referred to herein as a "primer target." A primer is a sequence of nucleotides that can bind to the primer target and, for example, a polymerase can utilize the primer as a starting point to replicate nucleotides of a target sequence. A primer and a corresponding primer target have complementary sequences of nucleotides. In some cases, this complementarity can be used to select certain nucleotides without PCR, based on a sequence they contain, for example, when a CRISPR system is used with guide DNA/RNA to select a set of nucleotides with a particular sequence.

In various implementations, digital data of a data file can be encoded as a series of nucleotides and one or more polynucleotide sequences can be generated that encode the digital data for the data file. Multiple polynucleotide sequences can be utilized to encode digital data of a single data file due to the segmentation of the digital data. In particular implementations, each polynucleotide sequence can encode an individual segment of the digital data. The portion of the polynucleotide sequence that encodes an individual segment of the digital data can be referred to herein as a payload region. The digital data can be segmented to ensure that the length of the polynucleotide sequences is less than a threshold length.

The polynucleotide sequences described in implementations herein can include regions to encode the digital data and regions encoding identifiers for the data file that includes the digital data being encoded. For example, the identifiers encoded by regions of the polynucleotide sequences can correspond to various groups of polynucleotide sequences that encode digital data for a particular data file. That is, for each data file, the digital data of the data file is encoded by one or more groups of polynucleotide sequences. Additionally, each polynucleotide sequence included in a particular group includes at least one region that encodes the same identifier. Further, the frameworks and techniques described herein can provide some structure around the quantity of polynucleotide sequences included in each group. To illustrate, the quantity of polynucleotide sequences included in each group can be substantially similar or the number of polynucleotide sequences included in each group can be within a specified range. In addition, the frameworks can include metadata indicating the particular group identifiers that encode the digital data of the data file.

The polynucleotide sequences can be generated by a computing system and represented by polynucleotide data.

The polynucleotide data can be used by a polynucleotide synthesizing machine to synthesize physical polynucleotides according to the polynucleotide sequence data. A polynucleotide data storage system can store the polynucleotides in one or more containers that may also contain a medium, such as a liquid. In particular implementations, polynucleotides can be stored in a liquid, such as water. Each container can store polynucleotides that encode digital data. In some cases, a container of the polynucleotide data storage system can store polynucleotides encoding digital data of a number of data files. For example, a container of a polynucleotide data storage system can store polynucleotides encoding digital data of a first data file and polynucleotides encoding digital data of a second data file (or more). Additionally, the data files that have polynucleotides stored in a container of the polynucleotide data storage system can have different amounts of data. Thus, the number of polynucleotides that encode digital data for the various data files can be different and, correspondingly, the number of groups of polynucleotides associated with each data file can also be different. Further, the quantity of polynucleotides included in each group, may be intentionally designed according to the frameworks and techniques described herein, to include relatively the same number of polynucleotides or similar numbers that are within a specified range.

In response to receiving a request to retrieve particular digital data, one or more polynucleotides can be identified that encode the requested digital data. For example, a memory structure that stores the metadata indicating the groups corresponding to the requested digital data can be accessed and the group identifiers associated with the requested digital data can be obtained. Primers can then be selected that are complementary to the group identifiers and the polynucleotides that encode the digital data can be selectively amplified using the primers and/or selectively sequenced. In situations where digital data from a plurality of data files is being requested, the primers complementary to the group identifiers corresponding to each of the plurality of data files can be identified. After amplification of the polynucleotides and/or sequencing of the amplification product, the polynucleotide sequencing data produced by the sequencing operations can be decoded to reproduce the requested digital data.

FIG. 1 is a schematic diagram of a process 100 to produce a framework for designing and storing polynucleotides that encode digital data as part of a polynucleotide data storage system. The process 100 can take place before the synthesis of polynucleotides that encode digital data.

At operation 102, the process 100 can include obtaining digital data 104. The digital data 104 can include a sequence of 1s and 0s that can be processed by a computing device. The digital data 104 can include input and/or output related to one or more applications. In illustrative implementations, the digital data 104 can be related to at least one of audio content, video content, image content, or text content. The digital data 104 can be associated with one or more data files.

At operation 106, the process 100 can include performing a segmentation process with regard to the digital data 104. The segmentation process can include dividing the digital data 104 into segments 108. The number of the segments 108 can be based at least partly on a number of bits included in the digital data 104. The number of the segments 108 can also be based at least partly on an encoding scheme used to encode the bits of the digital data 104 as nucleotides. Additionally, the number of the segments 108 can be based at least partly on a length of polynucleotides (e.g., 60 to 300 nucleotides) stored by the polynucleotide data storage system that minimizes the potential for the polynucleotides to form secondary structures. Further, the number of the segments 108 can be based at least partly on the different types of information encoded by the polynucleotides stored by the polynucleotide data storage system. In some implementations, the number of the segments 108 can be based at least partly on a combination of one or more of the number of bits included in the digital data 104, the encoding scheme used to encode the digital data 104 as nucleotides, the length of the polynucleotides stored by the polynucleotide data storage system, and the different types of information encoded by the polynucleotides of the polynucleotide data storage system.

In particular implementations, the encoding scheme utilized to encode the bits of the digital data 104 can affect the length of the segments 108 because, in some cases, more than one bit of the digital data 104 can be encoded by a single nucleotide. In these situations, the number of the segments 108 produced can be less than a number of the segments 108 produced when a single nucleotide encodes a single bit of the digital data 104. Additionally, the different types of information encoded by the polynucleotides can affect the length of the segments 108 because the digital data 104 that is encoded by the polynucleotides is encoded by the payload region of the polynucleotides, but other information such as error correction information and addressing information can also be encoded by the nucleotides of the polynucleotides. Thus, the more information encoded by various regions of the polynucleotides, the fewer nucleotides that can be dedicated to encoding the digital data 104 and a greater number of polynucleotides may be utilized to encode the digital data 104.

At operation 110, the process 100 can include encoding the digital data 104 as one or more sequences of nucleotides, such as the group of payload sequences 112. The encoding of the digital data 104 as the group of payload sequences 112 can be performed according to one or more techniques that associate one or more bits of the digital data 104 with one or more nucleotides. In some implementations, a first group of bits can be associated with a first nucleotide, a second group of bits can be associated with a second nucleotide, a third group of bits can be associated with a third nucleotide, and a fourth group of bits can be associated with a fourth nucleotide. In an illustrative example, a bit pair 00 can correspond to a first nucleotide, such as A; a second bit pair 01 can correspond to a second nucleotide, such as C; a third bit pair 10 can correspond to a third nucleotide, such as G; and a fourth bit pair 11 can correspond to a fourth nucleotide, such as T. In another illustrative example, the digital data 104 can be mapped to a base-4 string with each number in base-4 mapping to a corresponding letter representing a nucleotide. To illustrate, 0, 1, 2, and 3 can each map to one of A, C, G, or T. In an additional illustrative example, the digital data 104 can be mapped to a base-3 string with a nucleotide mapping to each number of the base 3 string (e.g., 0, 1, 2) based on a rotating code.

The encoding of the digital data at 110 can be performed, in some implementations, before performing the segmentation process at 106. For example, the encoding operations can be performed on the entire string of bits included in the digital data 104. In these implementations, the segmentation process at 106 can produce the group of payload sequences 112 instead of producing the bit segments 108. In other implementations, the encoding of the bits as nucleotides performed at 110 can take place at other points in the process 100.

At operation 114, the process 100 includes producing identifiers 116. Individual identifiers 116 can be used to identify individual groups of polynucleotide sequences that encode the digital data 104. The identifiers 116 can correspond to primers that are used to amplify, replicate and/or sequence polynucleotides that encode the digital data 104. In particular, one or more regions of polynucleotides produced according to implementations described herein can encode the identifiers 116 and comprise a primer target region of the polynucleotides. In these situations, the primers utilized in the polynucleotide data storage system can be complementary to at least a portion of the regions of the polynucleotides that encode the identifiers 116. In some implementations, the identifiers 116 can include a series of unique alphanumeric symbols that are encoded by nucleotides. In illustrative examples, the techniques utilized to encode the digital data 104 as nucleotides can be the same as those utilized to encode the identifiers as nucleotides. In various implementations, the identifiers 116 can be generated by a pseudo-random number generation algorithm. Also, primers used in polynucleotide sequence replication and amplification can be scored against a number of criteria that indicate the fitness of sequences of nucleotides to function as primers (including, for example, GC content and melting temperature). Primers having scores that indicate a particular fitness to function as primers can be added to a specific group of primers. The primers from the group of primers can be used in amplification and replication of polynucleotide sequences that encode digital data. Additionally, an amount of overlap between primer targets and payloads encoding digital data can be determined. Minimizing the amount of overlap between primer targets and payloads can improve the efficiency of polynucleotide replication and amplification. The bits of the digital data can be randomized to minimize the amount of overlap between payloads encoding the digital data and primer targets.

At operation 118, the process 100 includes assigning the identifiers 116 to the bit segments 108 or to the payload sequences 112. In particular, the bit segments 108 or the payload sequences 112 can optionally be divided into groups and each group can be assigned an individual identifier 116 (related payload sequences can thus have one or more identifiers/group identifiers). In situations where the digital data 104 has been encoded as nucleotides before assigning the identifiers 116, the individual payload sequences 112 can be grouped and assigned to respective identifiers 116. In instances where the digital data 104 has not been encoded as nucleotides before 118, the individual bit segments 108 can be grouped and assigned to respective identifiers 116. In an illustrative example, when the bit segments 108 have been encoded to produce the payload sequences 112 before assigning the identifiers 116, operation 118 can produce group assignments 120 that associate individual identifiers 116 with various groups of payload sequences 112. In another illustrative example, when the bit segments 108 have not been encoded as nucleotides before 118, operation 118 can produce group assignments 122 that associate individual identifiers 116 with various groups of the bit segments 108.

In some implementations, the number of groups included in the group assignments 120, 122 can be based on a number of factors. For example, the number of group assignments produced can be based on a number of primers utilized in a polynucleotide data storage system and a number of polynucleotides stored together. In various implementations, the number of polynucleotides stored together can correspond to the number of polynucleotides stored in a container of the polynucleotide data storage system. In some implementations, the number of bit segments 108 or the number of payload sequences assigned to each group identifier 116 can be approximately the same. In an illustrative example, each storage container has 1 million polynucleotide sequences (however, storage systems and containers can contain much larger numbers, for example, at least about 100,000,000,000 polynucleotide sequences can be stored per storage container in a storage system). Using 10,000 primers, two primers per group, one can have up to 5,000 groups, or 10,000 if the primers are the same in the beginning and the end of the polynucleotide sequences (for the retrieval of data encoded by the polynucleotides of the polynucleotide data storage system). Thus, there would be 100 polynucleotides sequences per group. In this illustrative example, the bit segments 108 or the payload sequences 112 can be divided into groups of about 100 in each group. Thus, in this example, the identifiers 116 can be associated with about 100 different polynucleotides stored in the polynucleotide data storage system. In other cases, the number of segments included in each group can be within a certain percentage of an average number. To illustrate, in a polynucleotide data storage system that utilizes a pool of 10,000 primers and includes a container that can store 1 million polynucleotides, an average number of segments that can be included in each group can be 100, but the number of segments included in each group can vary. In a particular illustrative example, the number of the bit segments 108 or the payload sequences 112 included in each group can be within a threshold amount of an average number. In some cases, the threshold amount can be a particular number, such as 100 bit segments 108 or payload sequences 112 greater than or less than the average number. In other cases, the number of the bit segments 108 or payload sequences 112 included in each group can be a percentage of the average number, such as within 10% of the average number. In particular implementations, the variation in the number of the bit segments 108 or the payload sequences 112 included in each group can correspond to minimizing differences between the rates of amplification when the groups are amplified together.

In various implementations, the identifiers 116 can be assigned to groups of bit segments 108 or groups of payload sequences 112 that correspond to different data files. In some situations, the polynucleotides associated with the different data files can be designated as being stored in a same container of a polynucleotide data storage system. For example, the digital data 104 being stored in a polynucleotide storage system can include bits from a number of different data files. The number of data files associated with a particular group of identifiers 116 can be based at least partly on the number of polynucleotides designated to be stored in a container of a polynucleotide data storage system and a number of polynucleotides utilized to encode the digital data of each file. Thus, if a container of a polynucleotide data storage system stores 1 million polynucleotides, the total number of polynucleotides encoding one or more data files will be less than or equal to 1 million. To illustrate, a first data file can be encoded by 600,000 polynucleotides stored in a container of the polynucleotide data storage system and a second data file can be encoded by 400,000 polynucleotides stored in the container of the polynucleotide data storage system.

In particular situations, a set of the identifiers 116 associated with a particular group of the bit segments 108 or a particular group of the payload sequences 112 can be different from additional sets of the identifiers 116 associated with other groups of the bit segments 108 or the payload sequences 112. For example, a first set of the identifiers 116 can be associated with a first group of the bit segments 108 or a first group of the payload sequences 112 and a second, different set of the identifiers 116 can be associated with a second group of the bit segments 108 or a second group of the payload sequences 112. In this way, a first set of primers corresponding to the first set of the identifiers 116 can be utilized to amplify and/or sequence a first group of polynucleotides associated with the first group of the bit segments 108 or the first group of the payload sequences 112 and a second set of the identifiers 116 can be utilized to amplify and/or sequence a second group of polynucleotides associated with the second group of the bit segments 108 or the second group of the payload sequences 112. In various implementations, the first group of polynucleotides and the second group of polynucleotides can be stored in a same container of a polynucleotide data storage system. In these situations, the portions of the digital data 104 associated with the first group of polynucleotides can be selectively accessed using the first group of primers and not the second group of primers, while the portions of the digital data 104 associated with the second group of polynucleotides can be selectively accessed using the second group of primers and not the first group of primers. In some implementations, the first group and second group are associated with different data files.

In situations where the bit segments 108 have not been encoded as nucleotides before operation 118 takes place, the bit segments 108 can be encoded as nucleotides after the assigning of identifiers to the groups of bit segments that occurs at operation 118.

At operation 124, the process 100 includes generating polynucleotide data for a number of polynucleotide sequences. The polynucleotide data can be used as a template or design for synthesizing polynucleotide molecules that correspond to the polynucleotide data. The polynucleotide data can indicate a sequence of nucleotides that includes at least one region that encodes digital data. In an illustrative example, a representative polynucleotide sequence 126 can include a payload sequence 128 that encodes digital data 104. The payload sequence 128 can be included in the payload sequences 112 generated as part of operation 110. The polynucleotide sequence 126 can also include a group identifier region 130 that encodes one of the identifiers 116 that has been assigned to the payload sequence 128 at operation 118. In some instances, the identifier 116 corresponding to the group identifier region 130 can be encoded as nucleotides according to the same scheme utilized to encode the bit segments 108 as the payload sequences 112. In other situations, the identifier 116 corresponding to the group identifier region 130 can be encoded as nucleotides according to a different scheme than the scheme utilized to encode the bit segments 108 as the payload sequences 112. Other information can also be encoded by the nucleotides of the polynucleotide sequence 126. For example, universal regions or sequences can be encoded by one or more regions of the polynucleotide 126. These sequences can be used to simultaneously produce a copy of all polynucleotides 126 in the polynucleotide storage container. In another example, error correction information can be encoded by one or more regions of the polynucleotide 126. In another example, addressing information can be encoded by one or more regions of the polynucleotide 126. The addressing information can indicate a location within the digital data 104 for the particular bits encoded by the payload region. In one embodiment there is included a universal front region (universal front primer), followed by a group identifier (group identifier front primer), and then payload, with address and error correction information, followed by a group identifier (group identifier back primer) and then a universal region (universal back primer). In additional examples, a file identifier corresponding to a data file that includes at least a portion of the digital data 104 can be encoded by nucleotides of one or more regions of the polynucleotide sequence 126. In some implementations, the file identifier along with the identifiers of the respective groups can be utilized in the retrieval of the digital data 104. After the polynucleotide data has been generated for each polynucleotide, the polynucleotide data can be provided to an oligonucleotide synthesizer to synthesize the physical polynucleotides corresponding to the polynucleotide data produced at 124.

Figure 2:
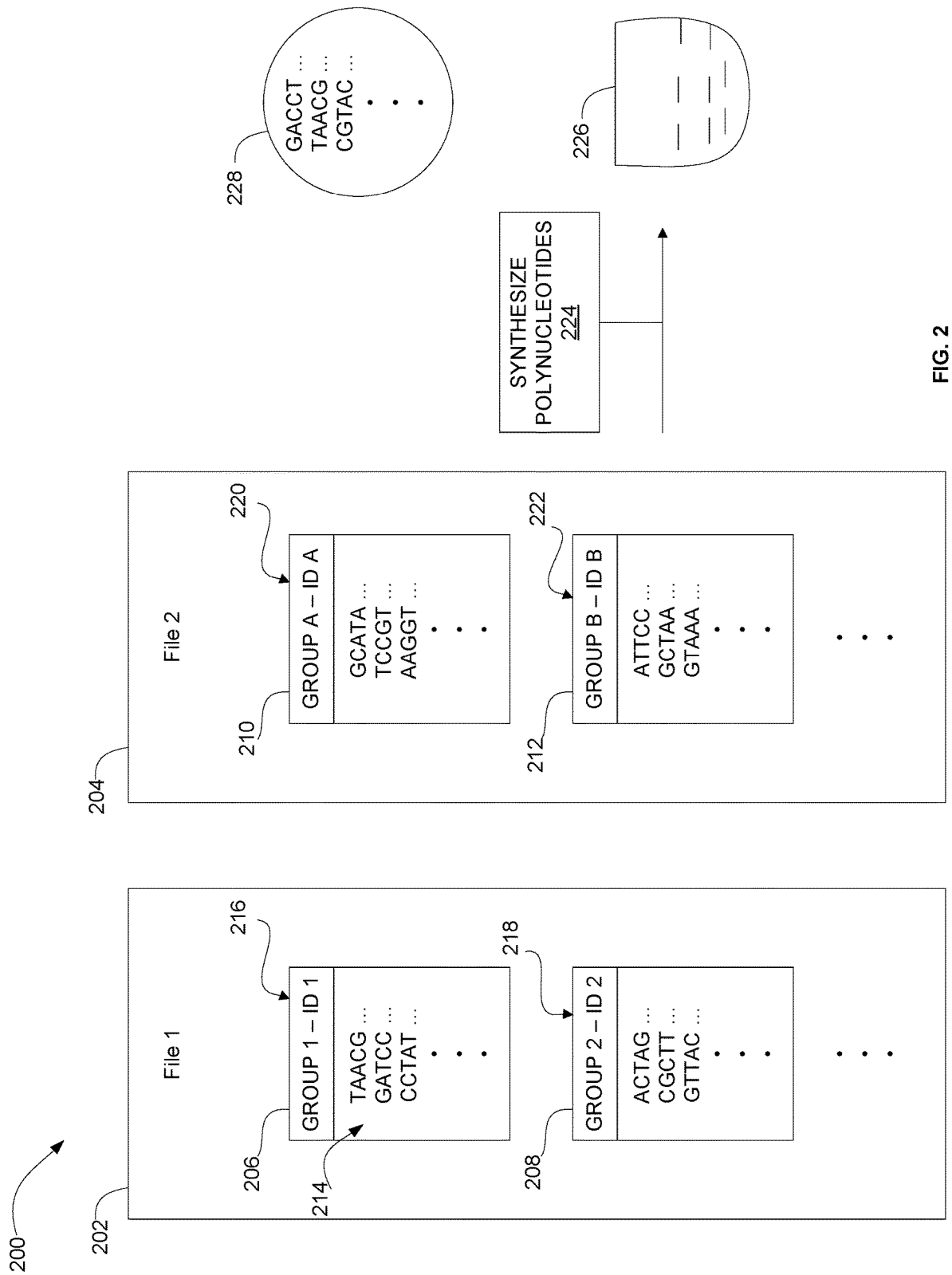
FIG. 2 shows a schematic diagram of a framework to store polynucleotides that encode digital data of different files.

FIG. 2 shows a schematic diagram of a framework 200 to store polynucleotides that encode digital data of different data files. In particular, the framework 200 includes a first data file 202 and a second data file 204. Although the illustrative example of FIG. 2 includes two data files, more data files can be included in the framework 200. Each data file 202, 204 can include digital data. The digital data of data files 202, 204 can be encoded using a number of polynucleotide sequences. For example, the first data file 202 can include first digital data that is encoded by a first group of polynucleotide sequences and the second data file 204 can include second digital data that is encoded by a second group of polynucleotide sequences. The number of polynucleotides sequences used to encode the digital data of the first data file 202 and the digital data of the second data file 204 can be different. In some cases, the number of polynucleotide sequences used to encode the digital data of the first data file 202 and the digital data of the second data file 204 can be based at least partly on the respective number of bits included in the first data file 202 and the second data file 204.

The polynucleotide sequences that encode the digital data of the first data file 202 and the digital data of the second data file 204 can be arranged in a single group or in a number of groups. The illustrative example of FIG. 2 shows that the polynucleotide sequences encoding the digital data of the first data file 202 can be arranged into at least a first group 206 and a second group 208. In addition, the illustrative example of FIG. 2 shows that the polynucleotide sequences encoding the digital data of the second data file 204 can be arranged into at least a third group 210 and a fourth group 212. Individual groups of polynucleotide sequences can include a particular number of polynucleotide sequences, such as representative polynucleotide sequence 214. The representative polynucleotide sequence 214 can include at least a payload region. The representative polynucleotide sequence 214 can also include additional regions that encode other information, such as a region to encode the group identifier 216, a region to encode addressing information, a region to encode an identifier of the first data file 202, a region to encode error correction information, a region to encode a universal primer or combinations thereof, and the like. In some implementations, the individual groups of polynucleotide sequences can include a same number of polynucleotide sequences. In other implementations, the individual groups of polynucleotide sequences can include a number of polynucleotide sequences in a specified range. In particular implementations, the specified range can indicate an average number of polynucleotide sequences to include in each group, a maximum threshold number above the average number, and a minimum threshold number below the average number.

Additionally, individual groups of polynucleotides can have a corresponding identifier. For example, the first group 206 can have a first identifier 216, the second group 208 can have a second identifier 218, the third group 210 can have a third identifier 220, and the fourth group 212 can have a fourth identifier 222. The identifiers 216, 218, 220, 222 can be represented by nucleotides included in one or more regions of the polynucleotide sequences associated with the respective groups 206, 208, 210, 212.

In various implementations, the information associated with the first data file 202 and the second data file 204 can be stored in a data storage structure. For example, the information associated with the first data file 202 and the second data file 204 can be stored on one or more computer-readable media as a table, array, record, tree, linked list, or combinations thereof. To illustrate, the polynucleotide sequences of the first group 206 can be stored in association with the first identifier 216, the polynucleotide sequences of the second group 208 can be stored in association with the second identifier 218, the polynucleotide sequences of the third group 210 can be stored in association with the third identifier 220, and the polynucleotide sequences of the fourth group 212 can be stored in association with the fourth identifier 222. In some implementations, the first file 202 can be represented by a first file identifier and the information of the first data file 202 can be stored in association with the first file identifier and the second file 204 can be represented by a second file identifier and the information of the second data file 204 can be stored in association with the second file identifier. In particular implementations, the first file identifier and the second file identifier can be represented as respective polynucleotide sequences, as a series of bits, or both. In various implementations, the first data file 202 and the second data file 204 can be associated with multiple file identifiers.

In particular implementations, at least a portion of the information associated with the first data file 202 and the second data file 204 can be stored as metadata of the first data file 202 and metadata of the second data file 204. The metadata can by utilized to selectively access the digital data encoded by the payload sequences of the groups corresponding to a particular data file. For example, a file identifier corresponding to the first data file 202 and the group identifiers corresponding to the first data file 202 (e.g., the first identifier 216 and the second identifier 218) can be utilized to access the digital data of the first data file 202. In this way, file identifiers and group identifiers can be used in conjunction with one another to access digital data encoded by polynucleotides.

Additionally, at operation 224, the framework 200 can include synthesizing polynucleotides. In particular, the polynucleotide sequences included in the groups 206, 208, 210, 212 can be a design template used to synthesize polynucleotide molecules. The polynucleotides represented by the polynucleotide sequences included in the groups 206, 208, 210, 212 can be stored together in a container 226. In this way, the polynucleotides encoding digital data of different data files, such as polynucleotides encoding data of the first data file 202 and polynucleotides encoding data of the second data file 204, can be stored in the same container 226.

The framework 200 can also include a set of primers 228. The set of primers 228 can include individual primers that have nucleotide sequences that are complementary to the group identifiers 216, 218 associated with the first data file 202 and the group identifiers 220, 222 associated with the second data file 204. In particular illustrative examples, nucleotide sequences representing the group identifiers 216, 218, 220, 222 can serve as primer target regions of the polynucleotides stored in the container 226 and the set of primers 228 can include primers that are complementary to the polynucleotide sequences of the group identifiers 216, 218, 220, 222. By storing the information of the first data file 202 and the second data file 204 according to the implementations described herein, the information associated with each data file 202, 204 can be accessed in the retrieval of digital data encoded by polynucleotides. For example, when information of the first data file 202 is requested, primers from the set of primers 228 that correspond to the group identifiers associated with the first data file 202 (e.g., the first group identifier 216 and the second group identifier 218) can be identified. To illustrate, primers included in the set of primers 228 that are complementary to the first group identifier 216 and the second group identifier 218 can be selected. The selected primers can then be added to a sample of the polynucleotides included in the container 226 or to the container 226 itself along with additional materials utilized to amplify and/or sequence the polynucleotides associated with the first data file 202, such as PCR reagents that can include at least one polymerase, nucleotides, buffering agents, and the like. A sample of the amplification product can be sequenced and analyzed to reproduce the requested digital data of the first data file 202 in a manner that will be described in more detail with respect to FIG. 3. At least a portion of the set of primers 228 can be synthesized before receiving a request to obtain digital data from a data file 202, 204, in some cases, while in other situations, at least a portion of the set of primers 228 can be synthesized after receiving a request to obtain digital data from a data file 202, 204. Further, as several of the methods involved in retrieval of the digital data may destroy the polynucleotides in the storage containers, a method to generate copies of such polynucleotides is needed. In some embodiments, the polynucleotides are associated with universal regions (further discussed in FIG. 3) common to all polynucleotides in the storage container which universal regions are located at 5' and 3' ends of the polynucleotides. Primers which are complementary to these universal regions can then be used to make multiple copies (for example via PCR) of the polynucleotides in the storage system, so as to store identical sets of polynucleotides/storage systems for future use. The universal primers can also be included in the set of primers 228.

In some implementations, primers included in the set of primers 228 can also be complementary to file identifiers related to the first data file 202 and the second data file 204. In various implementations, the polynucleotides that encode digital data of the first data file 202 and the second data file 204 can include sequences that correspond to file identifiers of the first data file 202 and the second data file 204. In this way, the digital data of the first data file 202 and the second data file 204 that is encoded by polynucleotides can be selectively accessed by primers of the set of primers 228 that are complementary to both the file identifier sequences of the respective data files 202, 204 and the group identifiers 216, 218, 220, 220 of the data files 202, 204. In a particular illustrative example, a polynucleotide encoding digital data of the first data file 202 can include a file identifier sequence adjacent to a group identifier sequence. Additionally, a primer of the set of primers 228 can have a sequence that is complementary to the file identifier sequence and the group identifier sequence or a sequence that is complementary to at least a portion of the file identifier sequence and at least a portion of the group identifier sequence. Continuing with this example, in response to a request for digital data included in the first data file 202, this primer can be selected from the set of primers 228 to amplify and/or sequence the polynucleotide that encodes a portion of the digital data of the first data file 202.

Figure 3:
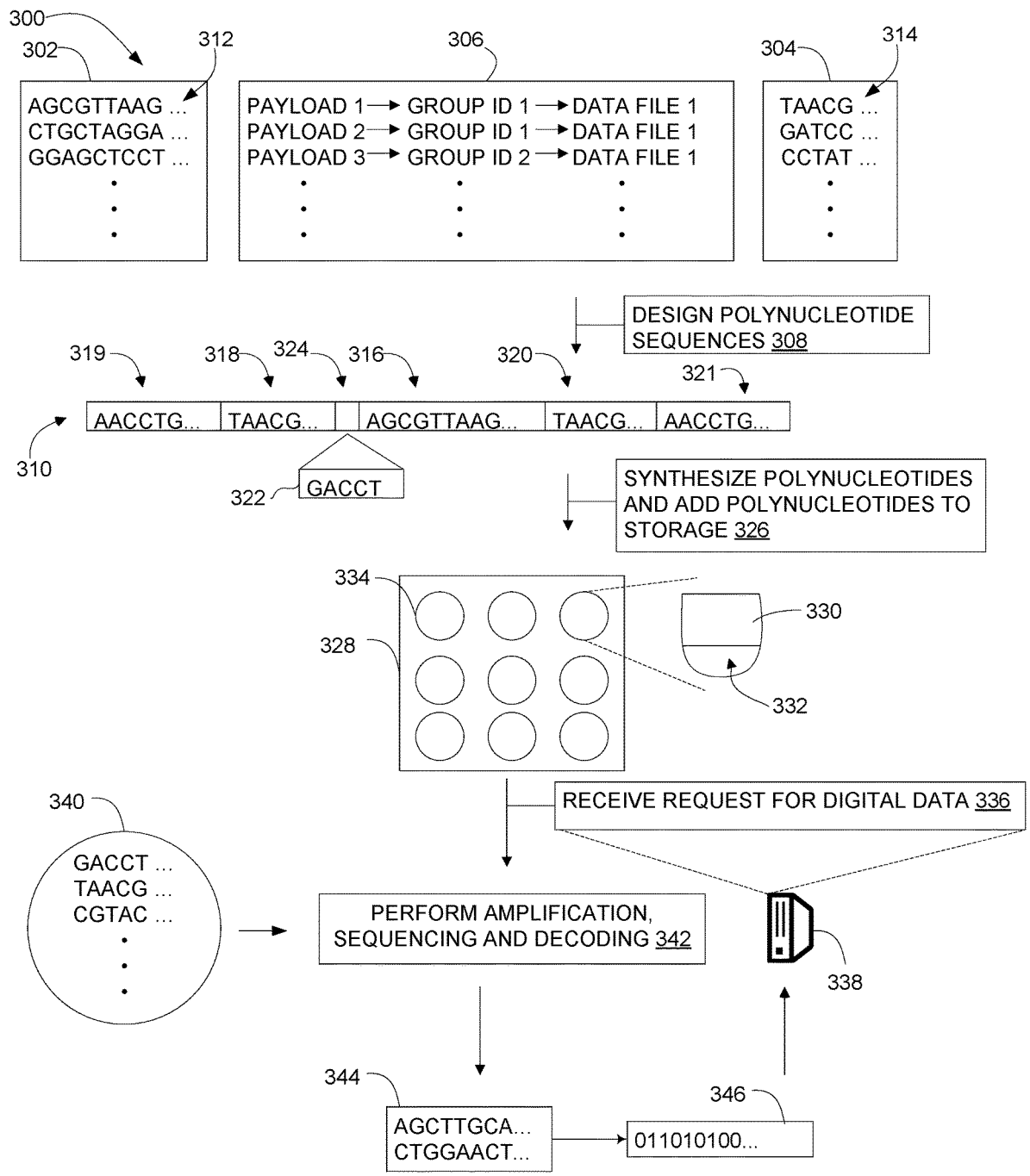
FIG. 3 shows a schematic representation of an example process to design polynucleotides that can be used to store digital data and retrieve the digital data from a polynucleotide storage system.

FIG. 3 shows a schematic representation of an example process 300 to design polynucleotides that can be used to store digital data and retrieve the digital data from a polynucleotide storage system. In particular implementations, the sequences of the polynucleotides can be designed by executing computer-readable instructions of one or more computer software applications. The polynucleotides can be designed using a number of payloads 302 and a number of group identifiers 304. The number of payloads 302 can each encode data from one or more data files that include digital data. The group identifiers 304 can each correspond to a respective group of the payloads 302. In addition, metadata 306 can be used to indicate relationships between the payloads 302, the group identifiers 304, and data files for which the payloads 302 encode digital data. In the illustrative example of FIG. 3, the metadata 306 indicates that a first payload (Payload 1) and a second payload (Payload 2) are both associated with a first group identifier (Group ID 1). Additionally, in the illustrative example of FIG. 3, the metadata 306 indicates that a third payload (Payload 3) is associated with a second group identifier (Group ID 2). Further, in the illustrative example of FIG. 3, the metadata 306 indicates that the first payload, the second payload, the third payload, the first group identifier, and the second group identifier are associated with the same data file (Data File 1). Thus, in this illustrative example, the first payload, the second payload, and the third payload include sequences of nucleotides that encode digital data from the first data file. Additionally, the payloads that encode the digital data of the first data file are divided into at least two groups: a first group corresponding to the first group identifier (Group ID 1) and a second group corresponding to the second group identifier (Group ID 2). Payloads that encode the digital data can also all be placed in a single group.

At 308 operation, the process 300 includes designing polynucleotide sequences. In particular, the polynucleotide sequences can be designed using individual payloads 302 and their corresponding group identifiers 304. In a particular example, a representative polynucleotide sequence 310 can be designed with a payload 312 included in the payloads 302 and a group identifier 314 included in the group identifiers 304. Thus, the polynucleotide sequence can include a payload region 316 that includes the payload 312, a first group identifier region 318 that includes the group identifier 314, and a second group identifier region 320 that includes the group identifier 314 (an identifier 314 generally includes a front primer and a reverse primer; such that a front primer target site and the reverse primer target site are different parts of a pair). The first group identifier region 318 can be placed at a 5' end of the payload region 316 and the second group identifier region 320 can be placed at a 3' end of the payload region 316.

In some implementations, a representative sequence of 310 can be optionally designed to include universal sequences 319, 321. Thus, the polymeric sequence can include a payload region 316 that includes the payload 312, a first group identifier region 318 that includes the group identifier 314, a second group identifier region 320 that includes the group identifier 314, a first universal sequence 319, and a second universal sequence 321. A universal sequence 319 can be placed at the 5' end of the polynucleotide sequence 310 and a universal region 321 can be placed at a 3' end of the polynucleotide sequence 310. In one embodiment, the same universal regions 319 and 321 are present in all polynucleotides in the container 330 (identical 5' universal region 319 sequences on all polynucleotides and identical 3' universal region 321 sequences on all polynucleotides). The universal regions 319 and 321 can correspond to primers that can be used to amplify and replicate or copy the whole pool of polynucleotides in storage container 330. Thus, a single primer pair (e.g., universal primers, which can be included in a set of primers 340) corresponding to the universal regions 319 and 321 can anneal and amplify/replicate every polynucleotide in the container 330 (or storage system 328), so as to make a copy (or copies) of all polynucleotides present at once (whole pool amplification of polynucleotides). The universal regions 319 and 321 can be synthesized on polynucleotides or they can be ligated after the polynucleotides are formed, as they are the outer most sequences and all universal regions 319 and 321 can be the same on each polynucleotide. This configuration results in nested primer sequences on all polynucleotides (universal region with nested group identifier region).

Thus, at 342, the process 300 can include amplification (copying) of all polynucleotides using primers 340 that correspond to the universal regions 319 and 321. Amplification of the polynucleotides can produce a complete copy (or copies) of all polynucleotides present. The copies of polynucleotide can then be separated/aliquoted into multiple containers 330 and/or storage systems 328 for future use (future request for digital data). This system allows for replication of the polynucleotides for distribution and/or replenishing the polynucleotides (for, example, in instances where sequencing of the polynucleotide is destructive and/or more copies are needed). Thus, in this system amplification of all polynucleotides (with universal regions 319 and 321) and selective amplification of polynucleotides corresponding to the requested/desired digital data can be carried out on a single pool of polynucleotides. These processes can both be carried out by PCR, either individually, sequentially or at the same time.

In some implementations, additional nucleotides 322 can be included in an additional region 324 of the polynucleotide sequence 310. In some examples, at least a portion of the additional region 324 can include nucleotides that encode a file identifier corresponding to the payload 312, such as nucleotides that encode an identifier for Data File 1. In other examples, at least a portion of the additional region 324 can include nucleotides that encode addressing information that indicates a location of the bits encoded by the payload 312 within the digital data file. In another example, at least a portion of the additional region 324 can include nucleotides that encode error correction information. Although the position of the additional region 324 is shown between the first group identifier region 318 and the payload region 316, the additional region 324 can be located at one or more different positions of the polynucleotide sequence 310.

At operation 326, the process 300 includes synthesizing polynucleotides and adding the polynucleotides to a polynucleotide storage system 328. The polynucleotides can be synthesized using the polynucleotide sequences designed at 308. Synthesizing the polynucleotides can include chemically bonding the nucleotides represented by the polynucleotide sequences, such as polynucleotide sequence 310, together in a linear chain. In some implementations, the polynucleotides can be synthesized by producing reactive forms of the individual nucleotides to be included in the polynucleotides and blocking certain functional groups by adding blocking molecules to the functional groups that are to be blocked from participating in reactions between the nucleotides. The non-blocked functional groups can be used to chemically join the nucleotides and then the blocking molecules can be removed from the remaining functional groups. In some situations, reactivity of certain remaining functional groups can be reduced, such as through a capping process, and other processes, such as an oxidation process, can be performed to prepare the polynucleotides for storage.

The polynucleotide storage system 328 can include a number of containers, such as container 330. Container 330 can include a medium 332 that stores a number of different polynucleotides. The medium 332 can include any medium that can maintain the chemical bonding and structure of polynucleotides over an extended period of time, such as several years, several decades, or longer. In some implementations, the medium 332 can include water, a pH buffered solution or a salt solution. Additionally, in other implementations, the polynucleotide storage system 328 can store polynucleotides using a media free arrangement, such as storing dried polynucleotide pellets.

In some implementations, the container 330 can store multiple copies of a polynucleotide. Additionally, in various implementations, more than one of the containers of the polynucleotide storage system 328 can store a particular polynucleotide. To illustrate, the container 330 and an additional container 334 of the polynucleotide storage system 328 can each store separate copies of a particular polynucleotide. In particular implementations, the polynucleotides stored in the polynucleotide storage system 328 can be stored according to the group identifiers of the polynucleotides. For example, a first number of polynucleotides that correspond to a first set of the group identifiers 304 can be stored in a first container of the polynucleotide storage system 328 and a second number of polynucleotides that correspond to a second set of the group identifiers 304 can be stored in a second container of the polynucleotide storage system 328. Also, the polynucleotides that encode data of a particular data file can be stored together. For example, the polynucleotides that encode the digital data for the Data File 1 can be stored in a particular container of the polynucleotide storage system 328, such as container 330. Further, polynucleotides that encode digital data for multiple data files can be stored in a particular container. To illustrate, container 330 can store polynucleotides of multiple data files, including the polynucleotides of Data File 1.

The polynucleotides stored in individual containers of the polynucleotide storage system 328, the group identifiers of polynucleotides stored in individual containers of the polynucleotide storage system 328, and/or the file identifiers related to polynucleotides stored in individual containers of the polynucleotide storage system 328 can be tracked and recorded. In this way, additional metadata can be generated that indicates the polynucleotides stored in the individual containers of the polynucleotide storage system 328. For example, additional metadata of the polynucleotide storage system 328 can indicate that polynucleotides associated with the first group identifier (Group ID 1), the second group identifier (Group ID 2), or both, are stored in the container 330. In other examples, additional metadata of the polynucleotide storage system 328 can indicate that polynucleotides associated with the first data file (Data File 1) are stored in the container 330.

At operation 336, the process 300 includes receiving a request for digital data. The request for digital data can be received from a computing device, such as computing device 338. After receiving the request for the digital data, the one or more polynucleotides that correspond to the digital data can be determined using a lookup table or other data structure that indicates the polynucleotides that encode the requested digital data. For example, the metadata 306 can be accessed and parsed to identify information for a data file being requested and the metadata 306 can be utilized to determine group identifiers and/or at least one file identifier for the data file. The group identifiers can correspond with primers that can be used to amplify and/or replicate the polynucleotides stored by the polynucleotide storage system 328. The primers that correspond to the group identifiers for one or more data files that include digital data being requested can be included in a set of primers 340. In some implementations, the primers are used to replicate/amplify the polynucleotides stored by the polynucleotide storage system 328 can be at least partially complementary to the group identifiers of the polynucleotides stored by the polynucleotides storage system 328. In some cases, the nucleotides included in at least a threshold number of positions of the primers included in the set of primers 340 can be complementary to at least a threshold number of positions of the group identifier regions associated with polynucleotides stored by the polynucleotide storage system 328. In this way, the primers of the set of primers 340 that correspond to the group identifiers of the requested digital data can be used to selectively amplify the polynucleotides that correspond to the digital data being requested. In various implementations, primers that correspond to a file identifier, as well as the group identifiers, can also be utilized to amplify the polynucleotides that encode requested digital data.

At operation 342, the process 300 can include amplification of polynucleotides corresponding to the requested digital data using primers of the set of primers 340 that correspond to the group identifiers and/or at least one file identifier associated with a data file that includes the digital data being requested. Amplification of the polynucleotides can produce an amplification product. At 342, the process 300 can also include, sequencing of the polynucleotides included in the amplification product and decoding the polynucleotides of the amplification product. In some implementations, the primers and enzymes used to selectively amplify the polynucleotides corresponding to the requested digital data can be added to one or more containers of the data storage system 328 or to one or more other containers outside of the polynucleotide storage system 328 that include the polynucleotides that correspond to the requested digital data.

In an illustrative example, PCR can be used to amplify the polynucleotides that correspond to the requested digital data. PCR can also be utilized during the sequencing of the polynucleotides. A PCR reaction has three main components: the template, the primers, and enzymes. The template is a single- or double-stranded molecule containing the (sub) sequence of nucleotides to be amplified. The primers are short synthetic strands that define the beginning and end of the region to be amplified. The enzymes include polymerases and thermostable polymerases such as DNA polymerase, RNA polymerase and reverse transcriptase. The enzymes create double-stranded polynucleotides from a single-stranded template by "filling in" complementary nucleotides one by one through addition of nucleoside triphosphates, starting from a primer bound to that template. PCR happens in "cycles," each of which increases, and can even double, the number of templates in a solution. The process can be repeated until the desired number of copies is created.

A variety of PCR techniques are known and can be used in the implementations described herein. PCR techniques are typically used for the amplification of at least a portion of a polynucleotide. The sample to be amplified is contacted with the first and second primers; a nucleic acid polymerase; and nucleotide triphosphates corresponding to the nucleotides to be added during PCR. Natural nucleotide triphosphates can include dATP, dCTP, dGTP, dTTP, and dUTP. Nucleoside triphosphates of non-standard nucleotides can also be added, if desired or needed. Suitable polymerases for PCR are known and include, for example, thermostable polymerases such as native and altered polymerases of *Thermus* species, including, but not limited to *Thermus aquaticus* (Taq), *Thermus flavus* (Tfl), and *Thermus thermophilus* (Tth), as well as the Klenow fragment of DNA polymerase I and the HIV-1 polymerase.

An additional type of PCR is Droplet Digital™ PCR (ddPCR™) (Bio-Rad Laboratories, Hercules, CA). ddPCR™ technology uses a combination of microfluidics and surfactant chemistry to divide PCR samples into water-in-oil droplets. The droplets support PCR amplification of the target template nucleotides they contain and use reagents and workflows similar to those used for most standard Taqman probe-based assays. Following PCR, each droplet is analyzed or read (by, for example, a droplet reader, such as those provided by Bio-Rad), to determine the fraction of PCR-positive droplets in the original sample. These data are then analyzed using Poisson statistics to determine the target concentration in the original sample. See Bio-Rad Droplet Digital™ (ddPCR™) PCR Technology.

While ddPCR™ is one PCR approach, other sample partition PCR methods based on the same underlying principles may also be used. The partitioned nucleotides of a sample can be amplified by any suitable PCR methodology that can be practiced within spdPCR. Illustrative PCR types include allele-specific PCR, assembly PCR, asymmetric PCR, endpoint PCR, hot-start PCR, in situ PCR, intersequence-specific PCR, inverse PCR, linear after exponential PCR, ligation-mediated PCR, methylation-specific PCR, miniprimer PCR, multiplex ligation-dependent probe amplification, multiplex PCR, nested PCR, overlap-extension PCR, polymerase cycling assembly, qualitative PCR, quantitative PCR, real-time PCR, single-cell PCR, solid-phase PCR, thermal asymmetric interlaced PCR, touchdown PCR, universal fast walking PCR, etc. Ligase chain reaction (LCR) can also be used.

Emulsion PCR can also be utilized in the implementations described herein. Emulsion PCR includes providing a water-in-oil emulsion that includes reagents used during the PCR process, such as a polymerase, primers, buffers, and the like. As the PCR process takes place, strands of the polynucleotides are replicated within the oil droplets using a polymerase and then denatured. The process continues for multiple cycles with replication of the new single stranded polynucleotides taking place within the droplets. The polynucleotides that have been produced during emulsion PCR can be recovered after breaking the emulsion and performing one or more separation processes. In some cases, beads can be used in emulsion PCR where polynucleotides bind to the surface of the beads within the emulsion and the replication of the polynucleotides takes place on the surface of the beads.

The amplification of polynucleotides can be performed using a thermocycler. A thermocycler (also known as a thermal cycler, PCR machine, or DNA amplifier) can be implemented with a thermal block that has holes where tubes holding an amplification reaction mixture can be inserted. The term "amplification reaction mixture" can refer to an aqueous solution comprising the various reagents used to amplify a target nucleic acid. The thermocycler can then raise and lower the temperature of the block in discrete, pre-programmed steps. Other implementations can utilize a miniaturized thermocycler in which the amplification reaction mixture moves via a channel through hot and cold zones on a microfluidic chip.

After the amplification process, one or more samples of the amplification product can be extracted and sequenced by a sequencing machine. The sequencing machine can provide raw sequence data output referred to herein as reads. Each position in a read is an individual nucleotide determined by the sequencing machine based on properties of the nucleotides sensed by components of the sequencing machine. A read can represent a determination of which of the four nucleotides—A, G, C, and T (or U)—in a strand of DNA (or RNA) is present at a given position in the sequence. The sequencing machine can produce polynucleotide data 344 that corresponds to the sequences of the polynucleotides read by the sequencing machine. The polynucleotide data 344 can be decoded using a reverse process that was used to encode the original digital data to produce a bit string 346 that corresponds to the original digital data being requested. The bit string 346 can be provided to the computing device 338 in response to the request for the digital data.

In some embodiments, the sequencing is coupled with retrieval (random access) of data (requested data). DNA storage systems can store multiple data objects or files physically together. When only part of these objects need to be retrieved, sequencing the entire pools captures all of the desired objects or file, but wastes resources reading/processing undesired data as well. Random-access via PCR or other methods selects only those files that need to be sequenced. Typically, the random-access process is done separately from sequencing procedures, which leads to unnecessary latency and complexity. Provided herein is a method whereby retrieval and sequencing are combined in a single method to yield the requested digital data (random access). For example, random access/retrieval of data can be accomplished in a single method by next generation sequencing (next generation sequencing (NGS); massively parallel sequencing in an automated process; Illumina®) with, for example, bridge amplification of the whole pool or part of the polynucleotides in the container 330. In this method, all of the polynucleotides in a container 330 can be amplified with the use of adapters, or part with the use of specific adapters, and bridge amplification, followed by sequencing with primers specific for the requested data (primers complementary to group identifier region 318 and/or 320). Alternatively, the file or group identifier region 318 and 320 can be complementary to the flow cell oligos used in bridge amplification and as well as the primer used in sequencing (to selectively amplify and sequence). In other embodiments, the universal sequences 319 and 321 can be used as adapters or primer targets sites for bridge amplification. This also works with other sequencing methods, such as nanopore sequencing, which can use CRISPR or beads to capture polynucleotide strands of interest, thus, random access can be done directly as part of sequencing with this method. Other methods that require strand capture and optional PCR amplification for the sequencing to be done, like those that read the electrical state of a system during DNA extension or those that use exonuclease to feed the sequencing system, can also be used in the methods described herein. One example of reading the electrical state of a system during DNA extension is Ion-torrent system. In brief, as a base is added, a single H+ ion is released, which is then detected by a CMOS-ISFET sensor (Rothberg, Jonathan M., et al. "An integrated semiconductor device enabling non-optical genome sequencing." Nature 475.7356 (2011): 348. Another sequencing method which may be used in the methods described herein is processive incorporation of deoxynucleoside triphosphate analogs by single-molecule DNA polymerase I (Klenow Fragment) nanocircuits (Kaitlin M. Pugliese et al. Journal of the American Chemistry Societ J. Am. Chem. Soc. 2015, 137, 9587-9594). Alternatively, one can use a flow-cell to selectively capture interested DNA. In brief, the DNA adapters on flow cell are extended with additional probe sequences, which are complementary to the targets and thus the DNA adapters/probe sequence can capture the target DNA (FIG. 1A of Shin et al. Nature Communications (2017) 8,14291 doi: 10.1038/ncomms14291). After capture of the target, one can the use sequencing primers to read the sequences. The methods described herein allow for sequencing to facilitate random access (retrieval of requested data and sequencing simultaneously).

Figure 4:
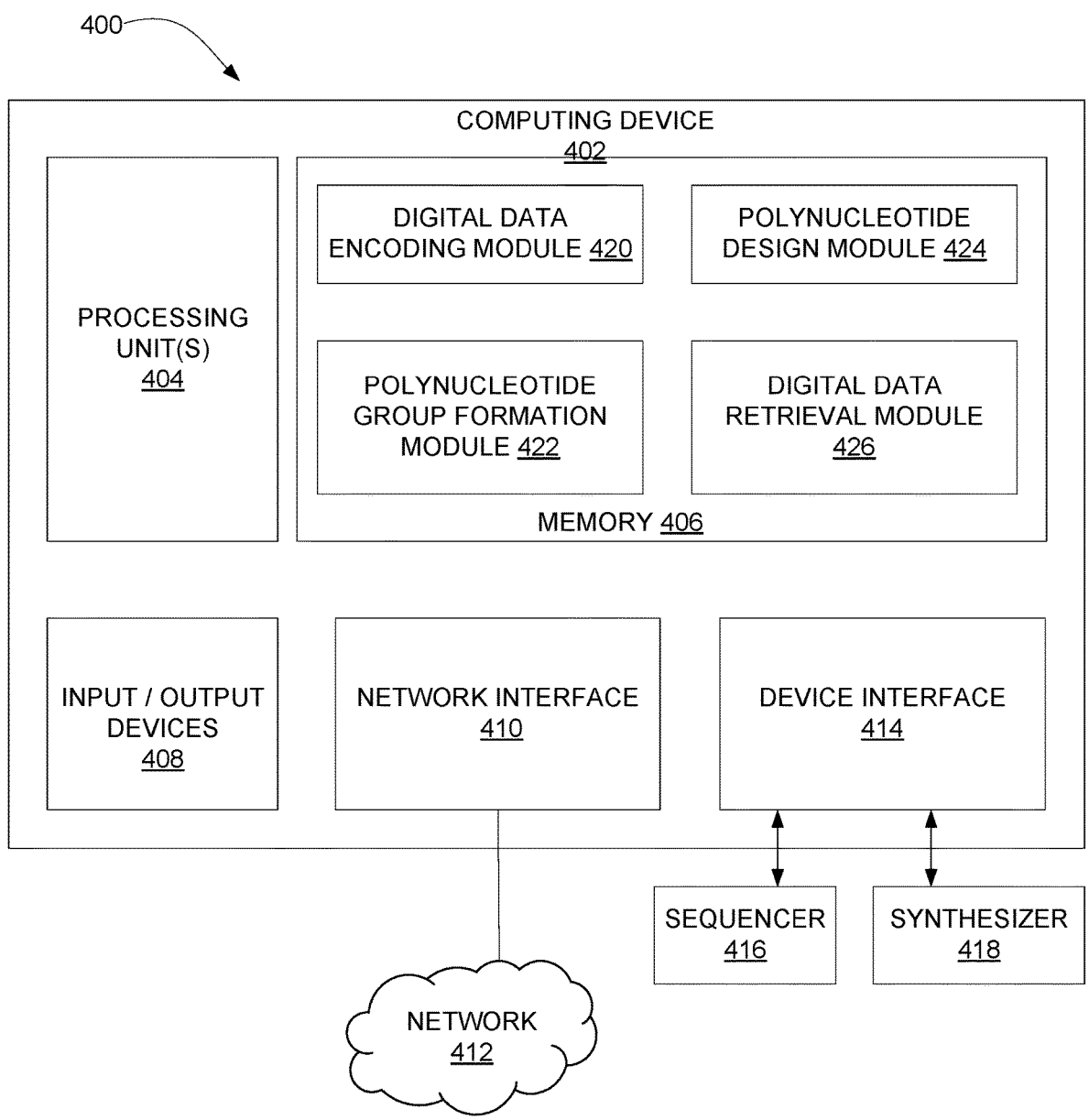
FIG. 4 shows a block diagram of an example computing device to produce a framework for designing polynucleotides that encode digital data and retrieving the digital data from the polynucleotides.

FIG. 4 shows a block diagram of an example system 400 including at least one computing device 402 to produce a framework for designing polynucleotides that encode digital data and retrieving the digital data from the polynucleotides. The computing device 402 can be implemented with one or more processing unit(s) 404 and memory 406, both of which can be distributed across one or more physical or logical locations. For example, in some implementations, the operations described as being performed by the computing device 402 can be performed by multiple computing devices. In some cases, the operations described as being performed by the computing device 402 can be performed in a cloud computing architecture.

The processing unit(s) 404 can include any combination of central processing units (CPUs), graphical processing units (GPUs), single core processors, multi-core processors, application-specific integrated circuits (ASICs), programmable circuits such as Field Programmable Gate Arrays (FPGA), and the like. In one implementation, one or more of the processing units(s) 404 can use Single Instruction Multiple Data (SIMD) parallel architecture. For example, the processing unit(s) 404 can include one or more GPUs that implement SIMD. One or more of the processing unit(s) 404 can be implemented as hardware devices. In some implementations, one or more of the processing unit(s) 404 can be implemented in software and/or firmware in addition to hardware implementations. Software or firmware implementations of the processing unit(s) 404 can include computer- or machine-executable instructions written in any suitable programming language to perform the various functions described. Software implementations of the processing unit(s) 404 may be stored in whole or part in the memory 406.

Alternatively, or additionally, the functionality of computing device 402 can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

Memory 406 of the computing device 402 can include removable storage, non-removable storage, local storage, and/or remote storage to provide storage of computer-readable instructions, data structures, program modules, and other data. The memory 406 can be implemented as computer-readable media. Computer-readable media includes at least two types of media: computer-readable storage media and communications media. Computer-readable storage media includes volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

In contrast, communications media can embody computer-readable instructions, data structures, program modules, or other data in a modulated data signal, such as a carrier wave, or other transmission mechanism. As defined herein, computer-readable storage media and communications media are mutually exclusive.

The computing device 402 can include and/or be coupled with one or more input/output devices 408 such as a keyboard, a pointing device, a touchscreen, a microphone, a camera, a display, a speaker, a printer, and the like. Input/output devices 408 that are physically remote from the processing unit(s) 404 and the memory 406 can also be included within the scope of the input/output devices 408.

Also, the computing device 402 can include a network interface 410. The network interface 410 can be a point of interconnection between the computing device 402 and one or more networks 412. The network interface 410 can be implemented in hardware, for example, as a network interface card (NIC), a network adapter, a LAN adapter or physical network interface. The network interface 410 can be implemented in software. The network interface 410 can be implemented as an expansion card or as part of a motherboard. The network interface 410 can implement electronic circuitry to communicate using a specific physical layer and data link layer standard, such as Ethernet or Wi-Fi. The network interface 410 can support wired and/or wireless communication. The network interface 410 can provide a base for a full network protocol stack, allowing communication among groups of computers on the same local area network (LAN) and large-scale network communications through routable protocols, such as Internet Protocol (IP).

The one or more networks 412 can include any type of communications network, such as a local area network, a wide area network, a mesh network, an ad hoc network, a peer-to-peer network, the Internet, a cable network, a telephone network, a wired network, a wireless network, combinations thereof, and the like.

A device interface 414 can be part of the computing device 402 that provides hardware to establish communicative connections to other devices, such as a sequencer 416, a polynucleotide synthesizer 418, etc. The device interface 414 can also include software that supports the hardware. The device interface 414 can be implemented as a wired or wireless connection that does not cross a network. A wired connection may include one or more wires or cables physically connecting the computing device 402 to another device. The wired connection can be created by a headphone cable, a telephone cable, a SCSI cable, a USB cable, an Ethernet cable, FireWire, or the like. The wireless connection may be created by radio waves (e.g., any version of Bluetooth®, ANT™, Wi-Fi® IEEE 802.11, etc.), infrared light, or the like.

The computing device 402 can include multiple modules that may be implemented as instructions stored in the memory 406 for execution by processing unit(s) 404 and/or implemented, in whole or in part, by one or more hardware logic components or firmware. The memory 406 can be used to store any number of functional components that are executable by the one or more processing units 404. In many implementations, these functional components can comprise instructions or programs that are executable by the one or more processing units 404 and that, when executed, implement operational logic for performing the operations attributed to the computing device 402. Functional components of the computing device 402 that can be executed on the one or more processing units 404 for implementing the various functions and features related to generating polynucleotide sequences for the storage and retrieval of digital data, as described herein, include a digital data encoding module 420, a polynucleotide group formation module 422, a polynucleotide design module 424, and a digital data retrieval module 426. One or more of the modules, 420, 422, 424, 426 can be used to implement frameworks 100, 200, and at least a portion of the process 300 of FIG. 1, FIG. 2, and FIG. 3.

The digital data encoding module 420 can include computer-readable instructions that are executable by the processing unit(s) 404 to encode digital data as a sequence of nucleotides. The digital data encoding module 420 can obtain digital data from one or more sources. In some cases, the digital data can also be stored by the memory 406. Also, the digital data can be stored by a data storage device coupled to, or otherwise accessible to, the computing device 402. The digital data can be related to image content, video content, text content, audio content, combinations thereof, and so forth. The digital data can include a bit string comprised of 1s and 0s. In some cases, the digital data can be included in a data file.

The digital data encoding module 420 can encode the 1s and 0s of the digital data as a sequence of nucleotides, such as A, T, G, C, or U. In particular implementations, each 1 or 0 of the digital data can be encoded as a particular nucleotide. In some cases, groups of 1s and groups of 0s of the digital data can be encoded as a particular nucleotide. In various implementations, the 1s and 0s of the digital data can be converted to a number in a number system other than base-2 before encoding. For example, the 1s and 0s of the digital data can be converted to a base-3 format or a base-4 format before encoding.

In illustrative implementations, the digital data encoding module 420 can encode the 1s and 0s of the digital data according to a binary encoding scheme. For example, the digital data encoding module 420 can encode the series of bits 00 as a first nucleotide (e.g., A), the series of bits 01 as a second nucleotide (e.g., T), the series of bits 10 as a third nucleotide (e.g., G), and the series of bits 11 as a fourth nucleotide (e.g., C).

In other illustrative implementations, the digital data encoding module 420 can encode the 1s and 0s of the digital data according to a ternary encoding scheme. For example, the digital data encoding module 420 can convert the 1s and 0s of the digital data to modified digital data comprising 0s, 1s, and 2s. Subsequently, the digital data encoding module 420 can encode the 0s, 1s, and 2s of the modified digital data as nucleotides. In some implementations, the data encoding module 420 can encode the 0s, 1s, and 2s of the modified digital data as nucleotides according to a preceding nucleotide in the sequence of nucleotides. To illustrate, a 0 preceded by G could be encoded as T, while a 0 preceded by A could be encoded as C.

In additional illustrative implementations, the digital data encoding module 420 can encode the 1s and 0s of the digital data according to a base-4 encoding scheme. In an example, the digital data encoding module 420 can convert the 1s and 0s of the digital data to modified digital data comprising 0s, 1s, 2s, and 3s. In these situations, when 4 nucleotides are used to encode the digital data, each type of nucleotide being used to do the encoding can correspond with a respective base-4 number. Thus, in a particular illustrative example, 0 can correspond with A, 1 can correspond with T, 2 can correspond with G, and 3 can correspond with C.

In some cases, the length of the sequences of nucleotides encoding the digital data can be limited. In illustrative implementations, the sequences of nucleotides used to encode digital data can have from 60 to 300 nucleotides, from 80 to 150 nucleotides, from 90 to 120 nucleotides, or from 100 to 140 nucleotides. In situations where multiple sequences are used to encode the digital data, the digital data encoding module 420 can divide the bits of the digital data into segments. The digital data encoding module 420 can encode each of the segments of the digital data as a separate sequence of nucleotides. In some cases, the segments can be the same length, while in other situations, the segments can have varying lengths. In implementations where the segments have different lengths, the length of the segments can be within a range of lengths. The range of lengths can be based at least partly on a probability that polynucleotides may lose a linear structure when the length is greater than an upper threshold length or when the length is less than a lower threshold length.

The polynucleotide group formation module 422 can include computer-readable instructions that, when executed by the processing unit(s) 404, can arrange polynucleotides that encode digital data into a number of groups. The polynucleotide group formation module 422 can also determine identifiers for each of the groups. In some instances, the group identifiers can be utilized to determine a data file that includes digital data being encoded by polynucleotides of one or more groups. For example, the polynucleotide group formation module 422 can assign one or more group identifiers to respective groups that include the polynucleotides that encode digital data of a data file. The polynucleotide group formation module 422 can also generate metadata that indicates the group identifiers that correspond to the data file.

In addition, the polynucleotide group formation module 422 can determine a quantity of polynucleotides to include in individual groups. For example, the polynucleotide group formation module 422 can determine a number of individual polynucleotides to include in individual groups. In some cases, the quantity of polynucleotides included in individual groups can be a range having an upper threshold and a lower threshold. In particular implementations, the quantity of polynucleotides included in individual groups can be within a range of a specified average number of polynucleotides to include in individual groups.

In some implementations, the polynucleotide group formation module 422 can determine that a number of polynucleotides included in a group is less than a threshold number of polynucleotides. In situations where the number of polynucleotides included in individual groups is the same number, the polynucleotide group formation module 422 can determine that the quantity of polynucleotides included in a group is less than the number specified for each individual group. Additionally, in implementations where individual groups include a quantity of polynucleotides within a specified range, the polynucleotide group formation module 422 can determine that the quantity of polynucleotides included in a group is less than a lower threshold of the range.

Based at least partly on determining that the quantity of polynucleotides included in a group is less than a threshold number, the polynucleotide group formation module 422 can generate sequences of filler polynucleotides for the group. The quantity of filler polynucleotides for the group can bring the total number of polynucleotides for the group to at least the threshold number. For example, the quantity of polynucleotides of individual groups can be specified as 9,000 to 11,000 and a particular group may have 8,500 polynucleotides. In this situation, the polynucleotide group formation module 422 can generate at least 500 filler polynucleotides to include in the group such that the total number of polynucleotides for the group is at least 9,000. In another example, the quantity of polynucleotides of individual groups can be specified as 10,000 and a particular group may have 9,750 polynucleotides. Continuing with this example, the polynucleotide group formation module 422 can generate 250 filler polynucleotides to bring the total number of polynucleotides included in the group up to 10,000.

The polynucleotide group formation module 422 can generate additional metadata that tracks the filler polynucleotides added to one or more groups. To illustrate, the polynucleotide group formation module 422 can generate additional metadata indicating the sequences of the filler polynucleotides that are included in particular groups. In this way, the additional metadata can be used to identify filler polynucleotides that can be removed during the decoding of polynucleotides when digital data is requested that is encoded by the other, non-filler, polynucleotides included in the group. In other implementations, the polynucleotide group formation module 422 can generate one or more sequences of nucleotides that indicates polynucleotides that are filler polynucleotides. Thus, polynucleotides that are decoded that include a sequence of nucleotides specifying a filler polynucleotide may be removed from consideration when reconstructing digital data from other polynucleotides included in the group.

The polynucleotide design module 424 can include computer-readable instructions that, when executed by the processing unit(s) 404, generate polynucleotide data that correspond to polynucleotides that encode digital data. The polynucleotide design module 424 can utilize data corresponding to payloads produced by the digital data encoding module 420 to generate the polynucleotide data. The polynucleotide design module 424 can also utilize data corresponding to group identifiers associated with the payloads to generate polynucleotide data. Additionally, the polynucleotide design module 424 can utilize data corresponding to file identifiers associated with the payloads to generate polynucleotide data.

The polynucleotide design module 424 can also produce data corresponding to polynucleotide sequences that include nucleotides in addition to the nucleotides comprising the group identifiers and payloads. For example, the polynucleotide design module 424 can include nucleotides in a polynucleotide sequence that correspond with addressing information for the payload. In situations where a string of bits is divided into a number of segments before being encoded as a sequence of nucleotides, addressing information can indicate the segment of the bit string that is being encoded by a particular payload sequence and the location of the segment within the bit string. The polynucleotide design module 424 can generate one or more nucleotides that encode the addressing information and add the nucleotides encoding the addressing information into a polynucleotide sequence. The group identifiers can also include nucleotides that correspond to a key that can be used to retrieve the digital data encoded by a payload of a polynucleotide. The polynucleotide design module 424 can also add nucleotides to a polynucleotide sequence that correspond to error correction information. Further, the polynucleotide design module 424 can add nucleotides to a polynucleotide sequence that correspond to a file identifier.

The polynucleotide data generated by the polynucleotide design module 424 can be used to synthesize molecules that include the polynucleotide sequences designed by the polynucleotide design module 424. In some implementations, the polynucleotide design module 424 can communicate polynucleotide data corresponding to the polynucleotide sequences to one or more devices, such as polynucleotide synthesizer 418, used to synthesize the polynucleotides. For example, the polynucleotide design module 424 can communicate polynucleotide data to a service provider that synthesizes polynucleotides via the one or more networks 412. In another example, the polynucleotide design module 424 can communicate polynucleotides to a device that synthesizes polynucleotides via the one or more networks 412 and/or to one or more devices (e.g., polynucleotide synthesizer 418) via the device interface 414.

The digital data retrieval module 426 can include computer-readable instructions that when executed by the processing unit(s) 404 can provide digital data in response to a request for the digital data. In some implementations, the digital data retrieval module 426 can receive a request to obtain digital data. For example, the digital data retrieval module 426 can receive a request for a data file including a digital image. The digital data retrieval module 426 can identify one or more group identifiers and/or at least one file identifier that correspond to the requested data. To illustrate, the digital data retrieval module 426 can parse a data structure, such as a lookup table, to identify the group identifiers that correspond to the requested digital data.

The digital data retrieval module 426 can communicate with one or more devices, such as via the device interface 414, to request the polynucleotides that correspond to the group identifiers. In some implementations, the one or more devices in communication with the digital data retrieval module 426 can be coupled to, or otherwise associated with, a polynucleotide data storage system. In various implementations, the digital data retrieval module 426 can provide to another computing device the group identifiers and/or at least one file identifier associated with the requested digital data to a computing device that can determine primers to be used to amplify and/or sequence the polynucleotides of the groups. In addition, the digital data retrieval module 426 can access metadata indicating a storage location (e.g., one or more container identifiers) within a polynucleotide storage system that store polynucleotides that correspond to the requested digital data. In particular implementations, the storage location can be identified based at least partly on matching the group identifiers associated with the requested digital data with the group identifiers associated with the containers of the polynucleotide data storage system. In some implementations, the digital data retrieval module 426 can provide the information regarding the primers used to amplify and/or sequence the polynucleotides corresponding to the requested digital data and/or the information regarding the storage location of the polynucleotides corresponding to the requested digital data to one or more additional computing devices, such as a computing device coupled with a polynucleotide data storage system.

The digital data retrieval module 426 can receive the sequences of the polynucleotides from one or more devices, such as sequencer 416, and decode the polynucleotides using a reverse process from the encoding performed by the digital data encoding module 420. For example, in implementations where 00 in a string of bits is encoded as A, the digital data retrieval module 426 can decode each A in the polynucleotide sequences as 00. The digital data retrieval module 426 can reproduce the bit string of the digital data being requested and provide the bit string to one or more devices that requested the digital data.

In some implementations, the digital data retrieval module 426 can identify filler polynucleotides that are to be removed during the decoding process. In some cases, the filler polynucleotides can be identified by the digital data retrieval module 426 comparing sequence data received from the sequencer to additional sequences included in metadata that indicate the filler polynucleotides. Based on the comparison, the digital data retrieval module 426 can determine polynucleotide sequences included in the sequencing data that correspond to filler polynucleotides and refrain from decoding the sequences of the filler polynucleotides. In other cases, the filler polynucleotides can be identified based at least partly on analyzing particular regions of polynucleotide sequences included in the sequencing data that indicate filler polynucleotides.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clauses

1. A method comprising: encoding a series of bits as a plurality of polynucleotide sequences, wherein the series of bits comprises digital data of a first data file; assigning at least one identifier to the plurality of polynucleotide sequences of the first data file; encoding a series of bits as a plurality of polynucleotide sequences, wherein the series of bits comprises digital data of a second data file; assigning at least one identifier to the plurality of polynucleotide sequences of the second data file, wherein the identifier for the polynucleotides encoding the first data file is different than the identifiers for the polynucleotides encoding the second data file polynucleotides; assigning a universal sequence to the polynucleotide sequences of the first and second data file, wherein the assigned universal sequence is the same for all polynucleotides; and generating polynucleotide sequence data that includes polynucleotide sequences with a payload region, the identifier as an identifier region, and the universal sequence.

2. The method of clause 1 further comprising polynucleotides for more than two data files, wherein the identifiers are different for each data file.

3. The method of clause 1 or 2 further comprising: synthesizing polynucleotides based at least partly on the polynucleotide sequence data; and storing the polynucleotides in a container of a polynucleotide data storage system.

4. The method of any one of clauses 1-3 further comprising: selecting at least one primer that corresponds to the nucleotides of the universal sequence and amplifying, using the primers, the polynucleotides in the container to produce an amplification product of all polynucleotides in the container.

5. The method of clause 4 further comprising: aliquoting the amplification product to additional containers in the storage system, thereby providing additional containers with identical polynucleotides.

6. The method of any one of clauses 1-5 further comprising: receiving a request for the digital data of the first or second data file; selecting at least one primer that corresponds to nucleotides of the identifier region for the first or second data file; amplifying, using the primers, a subset of polynucleotides in the container to produce an amplification product specific for the first or second data file; sequencing the amplification product to produce sequencing data that includes at least one polynucleotide sequence; and decoding the polynucleotide sequence.

7. The method any one of clauses 1-5 further comprising: receiving a request for the digital data of the first or second data file; selecting at least one primer or primer pair that corresponds to nucleotides of the identifier region for the first or second data file; optionally amplifying, using the primers, the polynucleotides in the container to produce an amplification product specific for the first or second data file; sequencing the amplification product or capturing the polynucleotides associated with the desired data file using at least one primer or primer pair that correspond to the nucleotides of the identifier region for the first or second data file and then sequencing the captured polynucleotide sequence to produce data that includes at least one polynucleotide sequence; and decoding the polynucleotide sequence.

8. The method of clause 7, wherein selecting the primers that correspond to the nucleotides of the identifier region for specific first or second data file includes: accessing metadata indicating individual identifiers that correspond to individual data files; and determining, based at least partly on the metadata, that the identifiers correspond to the data file.

9. The method of clause 7, wherein the polynucleotides are not amplified prior to sequencing.

10. The method of clause 7, wherein the polynucleotides are captured on a flow cell or beads.

11. The method of clause 7, wherein the polynucleotides are captured and sequencing is initiated with the primers.

12. A method comprising: encoding a series of bits as a plurality of polynucleotide sequences, wherein the series of bits comprises digital data of a data file, wherein there is more than one data file; assigning at least one identifier to the plurality polynucleotide sequences, wherein the identifier is unique to each data file; generating polynucleotide sequence data that includes polynucleotide sequences with a payload region and the identifier as an identifier region; synthesizing polynucleotides based at least partly on the polynucleotide sequence data; and storing the polynucleotides in a container of a polynucleotide data storage system; receiving a request for the digital data of at least one data file; selecting a at least one primer or primer pair that corresponds to nucleotides of the identifier region for the digital data of the data file requested, wherein the primer is used to select the polynucleotides for sequencing and/or for initiating sequencing of the polynucleotides of the digital data of the data file requested; sequencing, using the primer, the polynucleotides for the digital data of the data file requested; and decoding the polynucleotide sequence.

13. The method of clause 12, wherein prior to sequencing the polynucleotides of the digital data of the data file requested, all polynucleotides in the container are amplified.

14. The method of clause 12 or 13, wherein the polynucleotides further comprise a universal sequence or adapter sequences.

15. The method of clause 12, wherein selecting the primers that correspond to the nucleotides of the identifier region for the digital data of the data file requested includes: accessing metadata indicating individual identifiers that correspond to individual data files; and determining, based at least partly on the metadata, that the identifiers correspond to the data file.

16. A system comprising: one or more processing units; memory in communication with the one or more processing units, the memory storing computer-readable instructions that, when executed by at least one processing unit of the one or more processing units, perform operations comprising: generating data indicating a plurality of payload sequences, individual payload sequences of the plurality of payload sequences encoding a number of bits of a series of bits, the series of bits being associated with a data file; generating metadata indicating that the plurality of payload sequences are associated with a universal primer and that the plurality of payload sequences are associated with an identifier, wherein the metadata indicates a container of a polynucleotide storage system that stores polynucleotides that encode a series of bit; generating polynucleotide data indicating a polynucleotide sequence including a payload sequence, an identifier sequence corresponding to the identifier and a universal sequence; receiving a request to copy digital data of the data file; identifying, in response to the request and based at least partly on the metadata, the universal sequence associated with polynucleotides in the container and an identifier of the container; and sending, to a computing device, data indicating the universal sequence and the identifier of the container.

17. The system of clause 16 further comprising, receiving a request for digital data of the data file; identifying, in response to the request and based at least partly on the metadata, the identifier and the identifier of the container; and sending, to a computing device, data indicating the identifier and the identifier of the container.

18. The method of any one of clauses 1-11, wherein the at least one identifier to the plurality of polynucleotide sequences of the first data file and/or the second data file are a pair of primer target nucleotide sequences.

19. The method of clause 7, wherein the polynucleotides are amplified by polymerase chain reaction (PCR) with the least one primer or primer pair.

20. The method of clause 12, wherein the primer facilitates sequencing of the polynucleotides.

Conclusion

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention (especially in the context of the following claims) are to be construed to cover both the singular and the plural, unless otherwise indicated herein or clearly contradicted by context.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications (collectively "references") throughout this specification. Each of the cited references is individually incorporated herein by reference for their particular cited teachings as well as for all that they disclose.

The invention claimed is:

1. A method comprising:
generating polynucleotide sequence data that include:
a first set of polynucleotide sequences encoding a first data file that each have a first identifier region and a universal region, and
a second set of polynucleotide sequences encoding a second data file that each have a second identifier region and the universal region,
creating synthetic polynucleotides based at least partly on the polynucleotide sequence data;
receiving a request for the first data file;
performing combined random access of data on the synthetic polynucleotides and sequencing by bridge amplification thereby sequencing only the first set of polynucleotide sequences, wherein the universal region is complementary to flow cell oligos used in bridge amplification and a specific sequencing primer hybridizes only to the first identifier region thereby sequencing only the first set of polynucleotide sequences, wherein the sequencing produces sequencing data; and
reproducing the first data file by decoding the sequencing data.

2. The method of claim 1, further comprising: storing the synthetic polynucleotides in a container of a polynucleotide data storage system.

3. The method of claim 2, further comprising: amplifying, using polymerase chain reaction (PCR), the synthetic polynucleotides in the container to produce an amplification product of all polynucleotides in the container.

4. The method of claim 3, further comprising: aliquoting the amplification product to additional containers in the polynucleotide data storage system, thereby providing additional containers with identical synthetic polynucleotides.

5. The method of claim 1, further comprising: identifying the specific sequencing primer that corresponds to the nucleotides of the first identifier region by:
accessing metadata indicating individual identifiers that correspond to individual data files; and
determining, based at least partly on the metadata, that the identifiers correspond to the first data file.

6. The method of claim 1, wherein the synthetic polynucleotides are not amplified by polymerase chain reaction (PCR) prior to sequencing.

7. The method of claim 1, further comprising: providing the first data file to a computing device.

8. A method comprising:
generating polynucleotide sequence data that include polynucleotide sequences with a payload region, an identifier region, and a universal region;

synthesizing polynucleotides based at least partly on the polynucleotide sequence data;
receiving a request for a data file;
selecting an identifier region for the digital data of the data file requested;
introducing the polynucleotides into a flow cell, wherein the universal region is complementary to flow cell oligos used in bridge amplification;
performing combined random access of data and sequencing of only polynucleotides having a payload region that contains the digital data of the data file requested by introducing into the flow cell specific sequencing primers that are complementary to the identifier region corresponding to the data file, wherein the sequencing produces sequence data; and
reproducing the data file by decoding the sequence data generated by the sequencing.

9. The method of claim 8, further comprising amplifying the polynucleotides prior to performing the combined random access of data and sequencing.

10. The method of claim 8, wherein selecting the identifier region for the digital data of the data file further comprises:
accessing metadata indicating identifiers that correspond to individual data files; and
determining, based at least partly on the metadata, an identifier that corresponds to the data file.

11. The method of claim 8, further comprising: encoding digital data of a data file as a plurality of polynucleotide sequences, wherein the payload region contains the polynucleotide sequences that encode the data file.

12. The method of claim 8, wherein a sequence of nucleotides in the identifier region for the digital data of the data file is an identifier that is unique to the data file and distinguishes the data file from other data files.

13. The method of claim 8, wherein the synthetic polynucleotides are not amplified by polymerase chain reaction (PCR) prior to sequencing.

14. The method of claim 8, further comprising: providing the data file to a computing device.

15. A system comprising:
a polynucleotide synthesizer;
a sequencer;
a processing unit; and
memory in communication with the processing unit, the memory storing computer-readable instructions that, when executed by the processing unit, perform operations comprising:
generating polynucleotide data indicating a polynucleotide sequence including a payload sequence, an identifier sequence, and a universal sequence;
instructing the polynucleotide synthesizer to synthesize polynucleotides based on the polynucleotide data, wherein individual ones of the polynucleotides comprise one of the payload sequences, the identifier sequence, and the universal sequence;
a digital data retrieval module stored in the memory and configured to receive a request for a data file;
instructing the sequencer to perform combined random access of data and sequencing by bridge amplification wherein the universal sequence is complementary to flow cell oligos used in bridge amplification and a specific sequencing primer is complementary only to the identifier sequence thereby sequencing only polynucleotides having the identifier sequence, wherein the sequencing produces sequencing data; and
wherein the digital data retrieval module is further configured to reproduce the data file by decoding the sequencing data.

16. The system of claim 15, wherein the processing unit further performs operations comprising:
receiving a request to copy digital data of the data file;
identifying, in response to the request and based at least partly on metadata, the universal sequence associated with polynucleotides and an identifier; and
sending, to a computing device, data indicating the universal sequence and the identifier.

17. The system of claim 15, wherein the processing unit further performs operations comprising: generating polynucleotide sequence data comprising payload sequences encoding a data file.

18. The system of claim 15, wherein the identifier sequence is an identifier that is unique to the data file and distinguishes the data file from other data files.

19. The system of claim 15, wherein the processing unit further performs operations comprising: providing the data file to a computing device.

* * * * *